United States Patent
Lui et al.

[11] Patent Number: 5,874,656
[45] Date of Patent: Feb. 23, 1999

[54] PROCESS FOR PREPARING O-ALKYLFLUOROBENZENES

[75] Inventors: Norbert Lui; Michael-Harold Rock, both of Köln, Germany

[73] Assignee: Bayer Aktiengesellschaft, Leverkusen, Germany

[21] Appl. No.: 946,292

[22] Filed: Oct. 7, 1997

[30] Foreign Application Priority Data

Oct. 17, 1996 [DE] Germany .................. 196 42 868.8

[51] Int. Cl.$^6$ .................. C07C 21/18; C07C 209/00; C07C 43/02
[52] U.S. Cl. .................. 570/142; 564/412; 564/442; 568/656; 568/56
[58] Field of Search .................. 570/142; 564/412, 564/442; 568/656, 56

[56] References Cited

U.S. PATENT DOCUMENTS 5,306,849  4/1994  Lui et al. .

FOREIGN PATENT DOCUMENTS 4225763  2/1994  Germany .

*Primary Examiner*—Alan Siegel
*Attorney, Agent, or Firm*—Sprung Kramer Schaefer & Briscoe

[57] ABSTRACT o-Alkylfluorobenzenes are advantageously prepared by heating the corresponding chloroformates to from 70° to 200° C. in the liquid phase in the presence of hydrogen fluoride and in the presence of an inert diluent other than a halogenated alkane.

8 Claims, No Drawings

PROCESS FOR PREPARING O-ALKYLFLUOROBENZENES

The present invention relates to a liquid phase process for preparing optionally substituted o-alkylfluorobenzenes from substituted phenyl chloroformates.

BACKGROUND OF THE INVENTION

There are only few existing processes for preparing o-alkylfluorobenzenes which attract increasing interest as intermediates for active compounds. Blocking undesirable substitution positions by tertiary butyl groups permits the selective introduction of fluorine at aromatic nuclei by nitration, reduction, heating in the presence of fluoride ions (Baltz-Schiemann reaction) and removal of the butyl groups (J. Chem. Soc. Perkin Trans. I 1987, 1).

U.S. Pat. No. 5,306,849 discloses that some fluorobenzenes can be prepared from the corresponding chloroformates by heating in the presence of hydrogen fluoride and in the absence of solvents in yields of maximally 69%. Use of trichloro-trifluoroethane as solvent resulted in a significant worsening of the space-time yield and the conversion, even when the temperature was increased. Thus, 2,6-dimethylfluorobenzene could only be obtained in a yield of 40%.

SUMMARY OF THE INVENTION

This invention accordingly provides a process for preparing o-alkylfluorobenzenes of the formula (I)

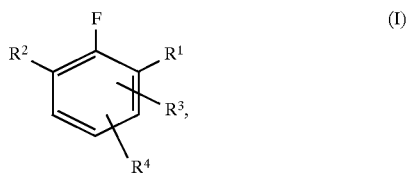

in which
$R^1$ is $C_1$–$C_6$-alkyl or $C_3$–$C_6$-cycloalkyl,
$R^2$ is hydrogen, $C_1$–$C_6$-alkyl or $C_3$–$C_6$-cycloalkyl,
$R^3$ and $R^4$ independently of one another are each hydrogen, halogen, $C_1$–$C_6$-alkyl, $C_3$–$C_6$-cycloalkyl, $C_1$–$C_6$-alkoxy, difluoromethoxy, trifluoromethoxy, chlorodifluoromethoxy, $C_1$–$C_6$-alkylthio, trifluoromethylthio, di-($C_1$–$C_4$-alkyl)-amino or phenyl,
which comprises heating chloroformates of the formula (II)

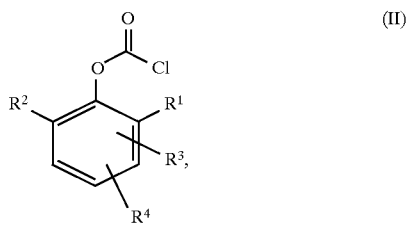

in which
$R^1$ to $R^4$ are each as defined in formula (I),
to from 70° to 200° C. in the liquid phase in the presence of hydrogen fluoride and in the presence of an inert diluent, other than a halogenated alkane.

DETAILED DESCRIPTION

Preferably, in the formulae (I) and (II),
$R^1$ is straight-chain or branched $C_1$–$C_4$-alkyl or $C_5$–$C_6$-cycloalkyl,
$R^2$ is hydrogen, straight-chain or branched $C_1$–$C_4$-alkyl or $C_5$–$C_6$-cycloalkyl and
$R^3$ and $R^4$ independently of one another are each hydrogen, fluorine, chlorine, bromine, straight-chain or branched $C_1$–$C_4$-alkyl, $C_5$–$C_6$-cycloalkyl, straight-chain or branched $C_1$–$C_4$-alkoxy, difluoromethoxy, trifluoromethoxy, chlorodifluoromethoxy, straight-chain or branched $C_1$–$C_4$-alkylthio, trifluoromethylthio, amino which is disubstituted by identical or different straight-chain or branched $C_1$–$C_4$-alkyl, or phenyl.

Particularly preferably
$R^1$ is methyl, ethyl, n-propyl or isopropyl,
$R^2$ is hydrogen, methyl, ethyl, n propyl or isopropyl and
$R^3$ and $R^4$ independently of one other are each hydrogen, fluorine, chlorine, bromine, methyl, ethyl, n-propyl or isopropyl, methoxy, difluoromethoxy, trifluoromethoxy, chlorodifluromethoxy, methylthio or phenyl.

The chloroformates of the formula II) required as starting materials for carrying out the process according to the invention are known or can be prepared similarly to known compounds.

The hydrogen fluoride required for the reaction should be as anhydrous as possible. Particularly suitable is the commercially available anhydrous hydrogen fluoride (100% strength hydrofluoric acid). For example 1 to 200 mol, preferably 1 to 100 mol, particularly preferably 2 to 50 mol, of hydrogen fluoride can be used per mole of chloroformate of the formula (II).

Preferred inert diluents for carrying out the process according to the invention are inert organic solvents with the exception of halogenated alkanes, it being possible to employ pure solvents or mixture thereof. The mixture with hydrogen fluoride may be a multi-phase system. Particularly preferred diluents are polychlorinated benzenes, for example dichlorobenzenes, in particular o-dichlorobenzene or the technical dichlorobenzene isomer mixture, trichlorobenzenes, in particular 1,2,3-trichlorobenzene or 1,2,4-trichlorobenzene or tetrachlorobenzenes, in particular 1,2,4,5-tetrachlorobenzene.

The amount of diluent employed for carrying out the process may be varied within a relatively wide range. Generally, 100 to 5000 ml, preferably 150 to 1000 ml, of diluent can be used per mole of chloroformate.

The process may, for example, b carried out by precharging diluent, hydrogen fluoride and chloroformate and heating to the reaction temperature. It is particularly advantageous to precharge the hydrogen fluoride and a part or the total of the diluent at reaction temperature a d to meter in the chloroformate which may optionally be dissolved in the other part of the diluent. In both instances, it is preferred to allow the hydrogen chloride formed and the carbon dioxide to escape from the reaction vessel via a pressure control unit.

Preference is given to reaction temperatures between 70° and 180° C. With regard to the reaction temperature, it is important for it to be at least as high as the temperature required to effect the decarboxylation of the chloroformate used. This minimum temperature can, if required, be easily determined by routine preliminary tests.

During the practice of the process according to the invention, the pressure has to be at least high enough for the reactant and the solvent to be maintained predominantly in the liquid phase at the respective reaction temperature. There is no critical upper limit for the pressure. It can be, for example, 0.5 to $10 \times 10^6$ Pa.

It is surprising that the yields can be increased significantly, as compared to the prior art, by the use of diluents according to the invention.

Surprisingly, the transalkylation which takes place in particular when trimethylphenyl chloroformates are decarboxylated in HF according to prior art processes is suppressed in the process according to the invention.

Examples

Example 1

1-Fluoro-2,4,6-trimethylbenzene

With stirring, 500 g of 2,4,6-trimethylphenyl chloroformate, 600 ml of 1,2,4-trichlorobenzene and 400 ml of HF were heated to 110° C. in a 2 l autoclave made of high-quality steel. The mixture was stirred for 6 hours at this temperature, and during this time the gases (hydrogen chloride and carbon dioxide) that formed were released via a brine-cooled condenser fitted with pressure relief valve ($2.5 \times 10^6$ Pa). The HF was then removed under reduced pressure and the residue was poured into water. The organic phase was separated off and dried over sodium sulfate. The product was purified by distillation. The solvent may be re-used.

Yield: 251 g (72% of theory)

Example 2

1-Fluoro-2,3-dimethylbenzene

The reaction was carried out using the method of Example 1, except that 220 g of 2,3-dimethylphenyl chloroformate, 500 ml of 1,2,4-trichlorobenzene and 600 ml of HF were heated to 140° C. and the gases formed were released at $2.8 \times 10^6$ Pa.

Yield: 113 g (76% of theory)

Example 3

1-Fluoro-2,4-dimethylbenzene

The reaction was carried out using the method of Example 1, except that 400 g of 2,4-dimethylphenyl chloroformate, 700 ml of trichlorobenzene and 400 ml of HF were heated to 150° C.

Yield: 192 g (71% of theory)

Example 4

1-Fluoro-2,6-dimethylbenzene

The reaction was carried out using the method of Example 1, except that 276 g of 2,6-dimethylphenyl chloroformate, 500 ml of 1,2,4-trichlorobenzene and 600 ml of HF were heated to 140° C.

Yield: 172 g (92% of theory)

What is claimed is:

1. A process for preparing o-alkylfluorobenzenes of the formula (I)

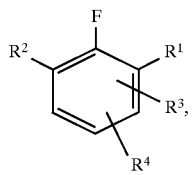

in which $R^1$ is $C_1$–$C_6$-alkyl or $C_3$–$C_6$-cycloalkyl, $R^2$ is hydrogen, $C_1$–$C_6$-alkyl or $C_3$–$C_6$-cycloalkyl, $R^3$ and $R^4$ independently of one another are each hydrogen, halogen, $C_1$–$C_6$-alkyl, $C_3$–$C_6$-cycloalkyl, $C_1$–$C_6$-alkoxy, difluoromethoxy, trifluoromethoxy, chlorodifluoromethoxy, $C_1$–$C_6$-alkylthio, trifluoromethylthio, di-($C_1$–$C_4$-alkyl)-amino or phenyl, which comprises heating chloroformates of the formula (II)

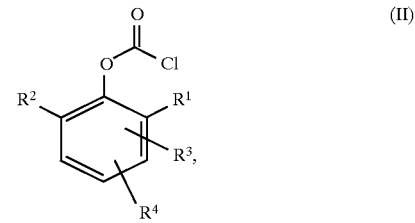

in which $R^1$ to $R^4$ are each as defined in formula (I), to from 70° to 200° C. in the liquid phase in the presence of hydrogen fluoride and in the presence of a polychlorinated benzene as diluent.

2. The process as claimed in claim 1, wherein in the formulae (I) and (II)

$R^1$ is straight-chain or branched $C_1$–$C_4$-alkyl or $C_5$–$C_6$-cycloalkyl, $R^2$ is hydrogen, straight-chain or branched $C_1$–$C_4$-alkyl or $C_5$–$C_6$-cycloalkyl and $R^3$ and $R^4$ independently of one another are each hydrogen, fluorine, chlorine, bromine, straight-chain or branched $C_1$–$C_4$-alkyl, $C_5$–$C_6$-cycloalkyl, straight-chain or branched $C_1$–$C_4$-alkoxy, difluoromethoxy, trifluoromethoxy, chlorodifluoromethoxy, straight-chain or branched $C_1$–$C_4$-alkylthio, trifluoromethylthio, amino which is disubstituted by identical or different straight-chain or branched $C_1$–$C_4$-alkyl, or phenyl.

3. The process as claimed in claim 1, wherein in the formulae (I) and (II)

$R^1$ is methyl, ethyl, n-propyl or isopropyl, $R^2$ is hydrogen, methyl, ethyl, n-propyl or isoproyl and $R^3$ and $R^4$ independently of one another are each hydrogen, fluorine, chlorine, bromine, methyl, ethyl, n-propyl or isopropyl, methoxy, difluoromethoxy, trifluoromethoxy, chlorodifluoromethoxy, methylthio or phenyl.

4. The process as claimed in claim 1, wherein 1 to 200 mol of hydrogen fluoride are employed per mole of chloroformate of the formula (II).

5. The process as claimed in claim 1, wherein 100 to 500 ml of diluent are employed per mole of chloroformate of formula (II).

6. The process as claimed in claim 1, wherein the process is carried out at 70° to 180° C.

7. The process as claimed in claim 1, wherein the pressure is at least high enough for the reactant and the solvent to be very predominantly in the liquid phase at the respective reaction temperature.

8. The process as claimed in claim 1, wherein the pressure is in the range from 0.5 to $10 \times 10^6$ Pa.

* * * * *